US006172124B1

(12) United States Patent
Wolflick et al.

(10) Patent No.: US 6,172,124 B1
(45) Date of Patent: *Jan. 9, 2001

(54) PROCESS FOR CONVERTING GAS TO LIQUIDS

(75) Inventors: John R. Wolflick, McKinney; Gary L. Beer, Plano; Richard L. Payne, McKinney, all of TX (US)

(73) Assignee: Sybtroleum Corporation, Tulsa, OK (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/950,312

(22) Filed: Oct. 14, 1997

Related U.S. Application Data

(63) Continuation of application No. 08/679,402, filed on Jul. 9, 1996, now abandoned.

(51) Int. Cl.[7] .................................................. C07C 27/00

(52) U.S. Cl. ......................... 518/705; 518/702; 518/703; 518/728

(58) Field of Search .................................. 518/702, 703, 518/705, 728

(56) References Cited

U.S. PATENT DOCUMENTS

| | | |
|---|---|---|
| 1,746,464 | 2/1930 | Fischer et al. . |
| 1,798,288 | 3/1931 | Wietzel et al. . |
| 2,247,087 | 6/1941 | Herbert . |
| 2,468,494 | 4/1949 | Griffin . |
| 2,472,427 | 6/1949 | Johnson . |
| 2,486,243 | 10/1949 | Atwell . |
| 2,500,533 | 3/1950 | Friedman . |
| 2,518,337 | 8/1950 | Krebs . |
| 2,552,308 | 5/1951 | Buchmann et al. . |
| 2,552,737 | 5/1951 | Rees ........................................ 48/214 |
| 2,579,828 | 12/1951 | Johnson ............................ 260/449.6 |
| 2,583,611 | 1/1952 | Sullivan . |
| 2,615,911 | 10/1952 | Williams . |
| 2,617,709 | 11/1952 | Cornell . |
| 2,640,843 | 6/1953 | Hill et al. . |
| 2,660,032 * | 11/1953 | Rosenthal ............................. 60/39.02 |
| 2,686,195 | 8/1954 | McAdams et al. . |
| 2,697,655 | 12/1954 | Dickinson et al. ..................... 48/196 |
| 3,549,335 | 12/1970 | Grotz . |
| 3,673,218 | 6/1972 | Cairns et al. . |
| 3,866,411 * | 2/1975 | Marion et al. ......................... 60/39.02 |
| 3,868,817 * | 3/1975 | Marion et al. ......................... 60/39.02 |
| 3,920,579 * | 11/1975 | Slater ..................................... 252/373 |
| 3,958,625 | 5/1976 | Wentorf, Jr. ............................. 165/2 |
| 3,959,972 * | 6/1976 | Rudolph et al. ......................... 60/651 |
| 3,986,349 * | 10/1976 | Egan . |
| 4,047,981 | 9/1977 | Slater . |
| 4,048,250 | 9/1977 | Garwood et al. . |
| 4,067,190 | 1/1978 | Hamm et al. ......................... 60/39.69 |
| 4,074,981 | 2/1978 | Slater . |
| 4,075,831 * | 2/1978 | McGann .............................. 60/39.05 |
| 4,092,825 * | 6/1978 | Egan . |
| 4,121,912 * | 10/1978 | Barber et al. ........................ 48/197 R |

(List continued on next page.)

FOREIGN PATENT DOCUMENTS

| | | |
|---|---|---|
| 83575/82 * | 12/1982 | (AU) . |
| 17172/92 * | 12/1992 | (AU) . |
| 29777/92 * | 6/1993 | (AU) . |
| 414019 | 6/1936 | (BE) . |
| 212755 * | 3/1987 | (EP) . |
| 103914 * | 1/1988 | (EP) . |
| 261771 | 3/1988 | (EP) . |
| 097425A | 1/1992 | (EP) . |
| 497425 | 8/1992 | (EP) . |
| 516441 | 12/1992 | (EP) . |
| 601886 | 6/1994 | (EP) . |
| 503482 | 7/1994 | (EP) . |
| 501331 * | 6/1995 | (EP) . |
| 871230 | 4/1942 | (FR) . |
| 922493 | 9/1947 | (FR) . |
| 1537457 | 8/1968 | (FR) . |
| 2103647 | 8/1984 | (GB) . |
| 2139644 | 11/1984 | (GB) . |
| 60-007929 | 1/1985 | (JP) . |
| 04364142 | 12/1992 | (JP) . |
| 4364142 | 12/1992 | (JP) . |
| WO86/05775 | 10/1986 | (WO) . |
| WO93/06041 | 4/1993 | (WO) . |
| WO95/24961 | 9/1995 | (WO) . |
| WO97/33847 | 9/1997 | (WO) . |

OTHER PUBLICATIONS

"Kinetics of the Fischer—Tropsch Synthesis using a Nitrogen–Rich Gas" T. Knutze et al; Oil Gas—European Mag.; Jan. 1995, pp. 19–24.

"A New Concept for the Production of Liquid Hydrocarbons from Natural Gas;" K. Hedden et al; Oil Gas—European Mag; Mar. 1994; pp. 42–44.

"Production of Synthesis Gas by Catalytic Partial Oxidation of Methane with Air" A.Jess et al; Oil Gas—European Mag; Apr. 1994, pp. 23–27.

(List continued on next page.)

Primary Examiner—Shailendra Kumar
Assistant Examiner—Jean F Vollano
(74) Attorney, Agent, or Firm—Baker Botts L.L.P.

(57) ABSTRACT

A process for converting a hydrocarbon gas (e.g. natural gas) to syngas which, in turn, is converted into a liquid hydrocarbon product wherein a substantial amount of the heat generated in the process is recovered for use in generating steam needed in the process or for conversion into mechanical energy. Further, tail gas produced by the process is used to fuel the gas turbine which, in turn, is used power the compressors needed for compressing the air used in the process. By using tail gas to fuel the gas turbine, less of the compressed combustion-air is needed to cool the combustion gases in the turbine and, instead, can be used to provide a portion of the process-air required in the process; thereby possibly saving up to 20 to 30 percent of the horsepower otherwise needed to compress the required volume of process-air.

4 Claims, 2 Drawing Sheets

U.S. PATENT DOCUMENTS

| | | | |
|---|---|---|---|
| 4,132,065 | * 1/1979 | McGann | 60/39.02 |
| 4,147,456 | 4/1979 | Klass . | |
| 4,158,680 | * 6/1979 | McGann | 261/149 |
| 4,184,322 | 1/1980 | Paull et al. | 60/39.02 |
| 4,309,359 | 1/1982 | Pinto . | |
| 4,315,893 | 2/1982 | McCallister . | |
| 4,338,292 | * 7/1982 | Duranleau | 423/656 |
| 4,341,069 | * 7/1982 | Bell . | |
| 4,345,915 | 8/1982 | Vakil et al. | 48/197 |
| 4,372,920 | 2/1983 | Zardi . | |
| 4,423,022 | 12/1983 | Albano et al. | 423/360 |
| 4,423,156 | 12/1983 | Bussemeier et al. | 518/717 |
| 4,434,613 | * 3/1984 | Stahl | 60/39.07 |
| 4,481,305 | 11/1984 | Jorn et al. | 518/705 |
| 4,492,085 | 1/1985 | Stahl et al. | 60/649 |
| 4,522,939 | 6/1985 | Minderhoud et al. . | |
| 4,524,581 | * 4/1984 | Cascone . | |
| 4,528,811 | 7/1985 | Stahl | 60/39.07 |
| 4,579,985 | 4/1986 | Minderhoud et al. . | |
| 4,579,986 | 4/1986 | Sie . | |
| 4,587,008 | 5/1986 | Minderhoud et al. . | |
| 4,618,451 | * 10/1986 | Gent | 252/373 |
| 4,640,766 | 2/1987 | Post et al. . | |
| 4,678,723 | 7/1987 | Wertheim . | |
| 4,681,701 | 7/1987 | Sie | 252/373 |
| 4,732,092 | * 3/1988 | Gould | 110/229 |
| 4,755,536 | 7/1988 | Mauldin et al. . | |
| 4,778,826 | 10/1988 | Jexl . | |
| 4,833,140 | 5/1989 | Weber et al. . | |
| 4,833,170 | 5/1989 | Agee . | |
| 4,869,887 | 9/1989 | Van Dijk . | |
| 4,894,205 | 1/1990 | Westerman et al. . | |
| 4,919,909 | 4/1990 | Lesur et al. . | |
| 4,946,477 | 8/1990 | Perka et al. | 48/197 R |
| 4,946,660 | 8/1990 | Denny et al. . | |
| 4,973,453 | 11/1990 | Agee . | |
| 4,999,029 | 3/1991 | Lueth et al. | 48/197 |
| 5,000,004 | 3/1991 | Yamanaka et al. | 60/723 |
| 5,026,934 | 6/1991 | Bains et al. | 585/314 |
| 5,028,634 | 7/1991 | Fiato | 518/707 |
| 5,048,284 | 9/1991 | Lywood et al. . | |
| 5,080,872 | 1/1992 | Jezl et al. | 422/201 |
| 5,126,377 | 6/1992 | Bessell | 518/714 |
| 5,177,114 | 1/1993 | Van Dijk et al. . | |
| 5,245,110 | * 9/1993 | Van Dijk . | |
| 5,295,350 | 3/1994 | Child et al. | 60/39.02 |
| 5,295,356 | 3/1994 | Billy | 62/20 |
| 5,324,335 | 6/1994 | Benham et al. | 44/452 |
| 5,472,986 | 12/1995 | Van Dijk . | |
| 5,477,924 | 12/1995 | Pollack . | |
| 5,500,449 | 3/1996 | Benham et al. | 518/700 |
| 5,504,118 | 4/1996 | Benham et al. | 518/719 |
| 5,506,272 | 4/1996 | Benham et al. | 518/700 |
| 5,520,891 | 5/1996 | Lee . | |
| 5,543,437 | 8/1996 | Benham et al. | 518/700 |
| 5,733,941 | 3/1998 | Waycuilis | 518/703 |
| 5,861,441 | 1/1999 | Waycuilis | 518/703 |

OTHER PUBLICATIONS

"Improve Syngas production using autothermal reforming"; T.S. Christensen; Hydrocarbon Processing; Mar. 1994; pp. 39–

Economical Utilization of Natural Gas to Produce Synthetic Petroleum Liquids; K. Agee et al; 75$^{th}$ Annual GPA Conv., Mar. 11–13, 1996; Denver CO.

International Search Report dated Oct. 17, 1997 re International Application PCT/US97/10733.

International Search Report dated Oct. 24, 1997 re International Application PCT/US97/10732.

International Search Report, dated Jun. 11, 1997 re International Application PCT/US 97/03729.

"The Fischer–Tropsch Synthesis," R.B. Anderson, Academic Press, Inc., NY, 1984, pp. 186–191.

Chemicals Produced in a Commercial Fischer–Tropsch Process, Industrial Chemicals Via C, Processes, Cpt. 2, M.E. Dry, American Chemical Society Journal, vol. 328, 1987.

"Conversion of Natural Gas to Liquid Fuels," R.C. Alden, The Oil and Gas Journal, Nov. 9, 1946, pp. 79–98.*

"Fischer–Tropsch Synthesis in Slurry Phase," M.d. Schlesinger, Industrial and Engineering Chemistry, Jun. 1951, pp. 1474–1479, Jun. 1985.*

"Advances in low temperature Fischer–Tropsch synthesis," B. Jager & R. Espinoza, Catalysis Today, vol. 23, 1995, pp. 17–28.*

"Fischer–Tropsch Processes Investigated at the Pittsburgh Energy Technology Center since 1944," M.J. Baird, R.R. Schehl & WIP. Haynes, Ind. Eng. Chem. Prod. Res. Dev. 1980, pp. 175–191.*

"Autothermal Reforming," Hydrocarbon Processing, Apr. 1984, p. 2.

"Produce Diesel from Gas," A.H. Singleton, Hydrocarbon Processing, May 1983, pp. 71–74.

"Make Syn Gas by Partial Oxidation," C.L. Reed and C.J. Kuhre, Hydrocarbon Processing, Sep. 1979, pp. 191–194.

"Malaysia, Shell Mull Gas to Products Project," Oil & Gas Journal, Sep. 16, 1985, p. 62.

"Process Makes Mid–distillates from Natural Gas," Oil & Gas Journal, Feb. 17, 1986, pp. 74–75.

"The Magic of Designer Catalysts," Gene Bylinsky, Fortune, May 27, 1985, pp. 82–88.

"The Mother Load of Natural Gas," R. Monasterskky, 150 Science News 298(1996).

"The Syntroleum Process," promotional flier, Aug. 1994.

"Hydrogen Process Broadens Feedstock Range," Industry & Economics News, 1960.

"Syn Gas from Heavy Fuels," C. J. Kubre and C.J. Shearer, 1971.

"Gasoline from Natural Gas," P.C. Keith, Jun. 15, 1946.

"Turbine–Powered, Synthesis–Gas System and Method," U.S. Ser. No. 08/814,780 (Provisional Application No. 60/013,225, filed Mar. 11, 1996), Mar. 10, 1997.

"Synthesis Gas Production System and Method," U.S. Ser. No. 08/879,553 (Provisional Application No. 60/020,092, filed Jun. 21, 1996), Jun 20, 1997.

"Combusing a Hydrocarbon Gas to Produce a Reformed Gas," by J. Waycuilis, U.S. Ser.No. 08/800,642 (CIP of 08/600,565–062754.0142), Feb. 14, 1997.

"Hydrogen Process Broadens Feedstock Range" Chemical Engineering, pp. 88, 90, 92. Jul. 09, 1962.

* cited by examiner

US 6,172,124 B1

PROCESS FOR CONVERTING GAS TO LIQUIDS

This application is a continuation of application Ser. No. 08/679,402 filed Jul. 9, 1996, now abandoned.

TECHNICAL FIELD

The present invention relates to a process for converting gases to liquids and in one of its aspects relates to a highly-efficient process for converting hydrocarbon gas (e.g. methane) to a hydrocarbon liquid (e.g. gasoline, distillates, etc.) which includes the improved operation for providing the required process-air and wherein waste heat and tail gas is efficiently recovered to be used within the process and/or to generate auxiliary power.

BACKGROUND ART

The desirability to convert light, hydrocarbon gases (e.g. natural gas) to liquids (e.g. methanol, gasolines, distillates, etc.) has long been recognized. Probably the most commonly-proposed process for carrying out this type of conversion is one wherein natural gas is first flowed through an Autothermal Reformer, e.g. a partial oxidation reformer, to convert the natural gas to a synthesis gas ("syngas", i.e. a gas comprised of carbon monoxide (CO) and hydrogen ($H_2$)). The syngas is then fed to a Fischer-Tropsch type of reactor which is loaded with an appropriate catalyst which, in turn, converts the syngas to a desired product (e.g. methanol, gasolines, distillates, etc.) depending on the catalyst and the operating conditions within the reactor. Such processes are well-known in the industry; for examples of Fischer-Tropsch ("F-T") processes of this type, see U.S. Pat. Nos. 1,798,288; 2,500,533; 2,552,308; 4,579,985; and 4,973,453.

While the type of basic process has been known for some time, efforts are continously being made to improve its efficiency in order to make it more commercially attractable. For example, where possible, air instead of oxygen is used as a reactant in the ATR stage since air is obviously cheaper and more readily available than pure oxygen; e.g. see U.S. Pat. Nos. 2,500,533; 2,552,308, et sec. Further, a continuing search is on-going to find the ultimate catalyst for use in the F-T reactor; e.g. see U.S. Pat. Nos. 5 4,522,939; 4,755,536; et sec. Also, improvements in the various elements (e.g. partial oxidation reformer) used in the process are important considerations in attempting to optimize the process (e.g. see U.S. Pat. Nos. 3,549,335; 4,778,826) for commerical use.

Another very important consideration in the commercialization of such a process is maximizing the recovery of otherwise wasted heat and gases from the process for use in the process, itself, or for generating excess energy (i.e. heat and/or mechanical power) which, in turn, can be sold or used in other applications. For example, (a) energy may be generated by reacting off-gas from the process in a fuel cell, see U.S. Pat. No. 4,048,250; (b) dry or tail gas may be used for, generating heat used in the process, see U.S. Pat. No. 4,048,250; (c) heat recovered from a gas turbine, which is used in the process to both compress the process-air and drive an electrical generator, may be used in the ATR, see U.S. Pat. No. 4,315,893; and (d) heat, recovered from the product after it passes through the reformer, may be used to generate a separate stream of superheated steam while the syngas may be expanded through a turbine to recover mechanical energy, see U.S. Pat. No. 4,074,981. While each of these approaches add to the operating efficiency of the overall conversion process, there is still much which can be done in the optimizing the process to make it more commercially acceptable.

SUMMARY OF THE INVENTION

The present invention provides a process for converting a hydrocarbon gas (e.g. natural gas) to syngas which, in turn, is converted into a liquid hydrocarbon product wherein a substantial amount of the heat generated in the process is recovered for use in the process or to be converted to mechanical energy. Further, the tail gas generated in the process is used to fuel the gas turbine which is used to power the compressors which, in turn, are used to compress the "process-air". By using tail gas to fuel the gas turbine, less of the compressed combustion-cooling air has to be used to cool the combustion gases (i.e. exhaust gases) from the combustor of the turbine and, instead, can be used to provide a portion of the process-air required in the process. This can save up to 20 to 30 percent of the horsepower which otherwise would be needed to compress the volume of process-air needed for the process.

More specifically, the present invention provides a process for converting a hydrocarbon feed gas to a hydrocarbon liquid wherein the process-air needed for carrying out the process is compressed by a compression unit which is powered by a gas turbine wherein the gas turbine has a compressor section, a combustor, and a turbine section. The compressor section compresses combustion-cooling air, a first portion of which (i.e. "combustion-air") is supplied to the combustor where it is mixed with tail gas which, in turn, is recovered from the process, itself.

A typical tail gas recovered from the present process is comprised of methane, carbon monoxide, carbon dioxide, hydrogen, nitrogen, and other light hydrocarbons (e.g. $C_2$-$C_4$) which burns substantially cooler than do higher-BTU fuels such as natural gas thereby producing combustion gases at lower temperatures. This allows a substantially smaller second portion of the compressed combustion-cooling air to be used to cool the the same volume of combustion gases to the temperature required for safe operation of the turbine section of the gas turbine. By using less of the compressed combustion-cooling air air for combustion and cooling, a substantial remaining portion (e.g. about 30 to 40% of the original volume) of the compressed combustion-cooling air from said compressor section can be supplied directly to said process to form a portion of the process-air required to carry out the present process.

Once the process air has been compressed, it is mixed with steam and is heated in a heater before the mixture is passed to an Autothermal Reforming Unit (ATR). A hydrocarbon feed gas (e.g. methane) is also mixed with steam and is heated in the heater (the heater possibly being fueled with tail gas from the process) before this feed gas/steam mixture is also passed into the ATR where it is mixed with the process air/steam mixture in the presence of a catalyst to form a syngas which, in turn, is comprised of nitrogen, carbon monoxide and hydrogen. Heat is recovered from the syngas and is used to generate steam, some of which is mixed with both the process-air and the feed gas.

The syngas is then passed over a catalyst in a Fischer-Tropsch reactor to thereby convert at least a portion of said syngas to liquid hydrocarbons. Heat is also recovered from the reactor as said syngas being converted to a liquid hydrocarbon and can be used in generating the steam needed in the present process. The products from the reactor are passed to a separation section where the unconverted syngas is separated from the liquid hydrocarbon. It is this unconverted syngas and by-products (methane, $C_2$–$C_4$, carbon dioxide, and nitrogen) which forms the "tail gas" which is used for fuel in the process. Also, at least a portion of the tail gas may be expanded through a turbine to recover mechanical energy therefrom.

BRIEF DESCRIPTION OF THE DRAWING

The actual construction, operation, and apparent advantages of the present invention will be better understood by referring to the drawings which are not necessarily to scale and in which like numerals refers to like parts and in which.

BEST KNOWN MODE FOR CARRYING OUT THE INVENTION

Figure 1:
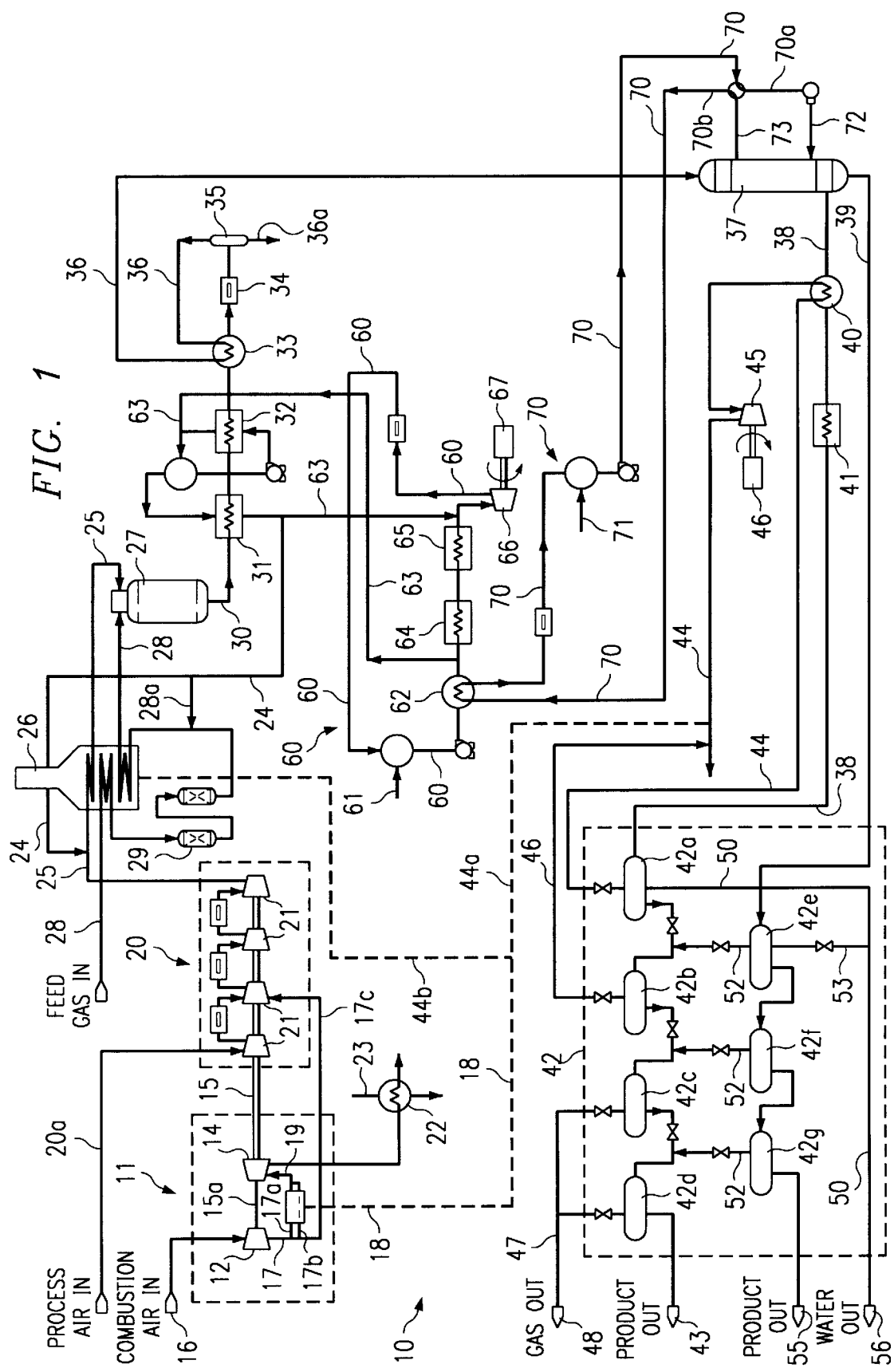
FIG. 1 is a schematic representation of an integrated gas conversion system for carrying out a process in accordance with the present invention.

Referring more particularly to the drawings, FIG. 1 discloses a schematical diagram of the system 10 which can be used in carrying out a conversion process in accordance with the present invention. Throughout the following description, examples of temperatures and pressures are given at respective stages of a process carried in accordance with the present invention. However, it should be recognized that these temperatures and pressures are only illustrative of the anticipated conditions within the system 10 and actual values may vary for any particular process without departing from the present invention. The recited conditions are based on a typical process in accordance with the present invention wherein 52.1 millon standard cubic feet of feed gas (e.g. natural gas) is processed per day.

System 10 is comprised of a standard gas turbine 11 (e.g. 32,500 horsepower) which furnishes power for compressing the air needed in the present process. As will be understood in the art, gas turbine 11 is comprised of a compressor section 12, a combustor section 13, and a power turbine section 14 which, in turn, has a primary power output shaft 15 for driving the process-air compressors and a secondary shaft 15a which drives compressor section 12 of gas turbine 11.

Figure 2:
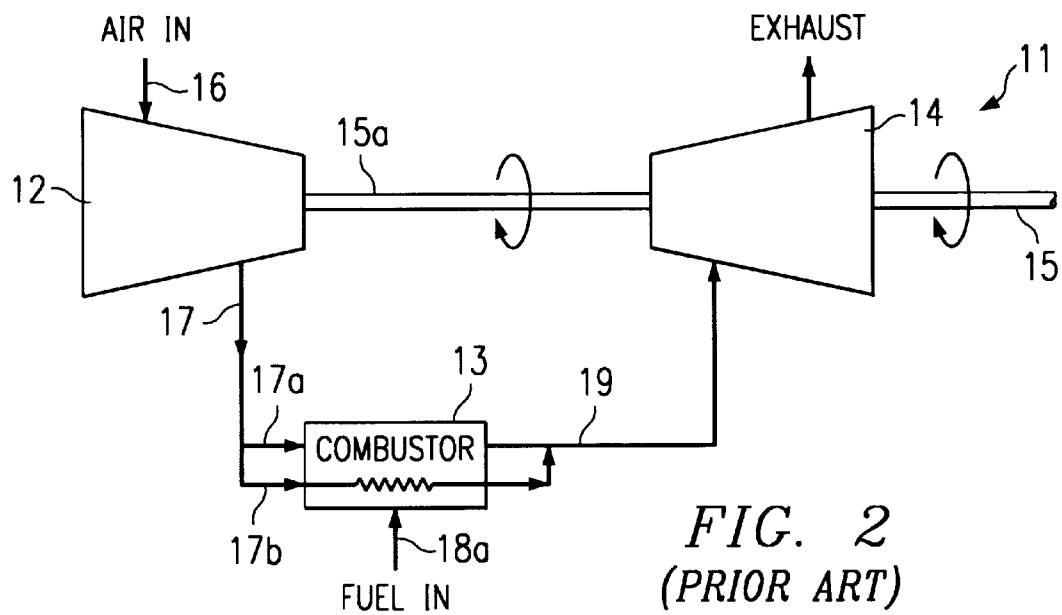
FIG. 2 is a schematic representation of a gas turbine as it is operated in the prior art.

As best seen in FIG. 2, in prior-art turbines of this type, air is supplied to the compressor section 12 of gas turbine 11 through inlet 16 at approximately atmospheric conditions (e.g. 14.7 psi and 80° F.) and is compressed before it is supplied to combustor 13 through line 17. A portion of the air (i.e. combustion-air) is fed to combustor 13 through line 17a where it is mixed with a high BTU fuel from line 18a and burned to produce a hot gas.

As will be understood in the art, when a high-BTU fuel such as natural gas (e.g. methane) is burned stochiometrically in a typical combustor in a gas turbine of this type, the resulting gases have a very high temperature (e.g. 2800° F.) which is too hot to be expanded through turbine section 14 without causing serious damage thereto. Accordingly, remaining air in line 17 from compressor section 12 (i.e. cooling air) is flowed through line 17b in heat exchange with combustor 13 to keep the combustion gases (i.e. exhaust) from combustor 13 at a temperature (e.g. 1800° F.) which can be safely handled by turbine section 14. The cooling air in line 17b is mixed with the combustion gases in line 19 from combustor 13 before the mixture is expanded through turbine section 14 to rotate shafts 15, 15a.

In accordance with one aspect of the present invention, the amount of air (i.e. cooling-air) needed for cooling the combustion gases to roughly the same temperatures as before (e.g. 1800° F.) is substantially reduced so that only a portion (e.g. about 60–70%) of the air compressed by the compressor section 12 will be used as combustion-cooling air, i.e. used for mixing with the fuel and for cooling of the combustion gases. This is accomplished by using the tail gas which is produced in the present process as fuel in place of a higher-BTU fuel such as methane. The tail gas which is comprised of methane, other light hydrocarbons, carbon monoxide, carbon dioxide, hydrogen, and substantial amounts of nitrogen produces the same quantity of combustion gases but at a significant lower temperature (e.g. 2100° F.); hence, less cooling is required to lower the gas temperature to that required (e.g. 1800°) for safe operation of turbine section 14.

Figure 3:
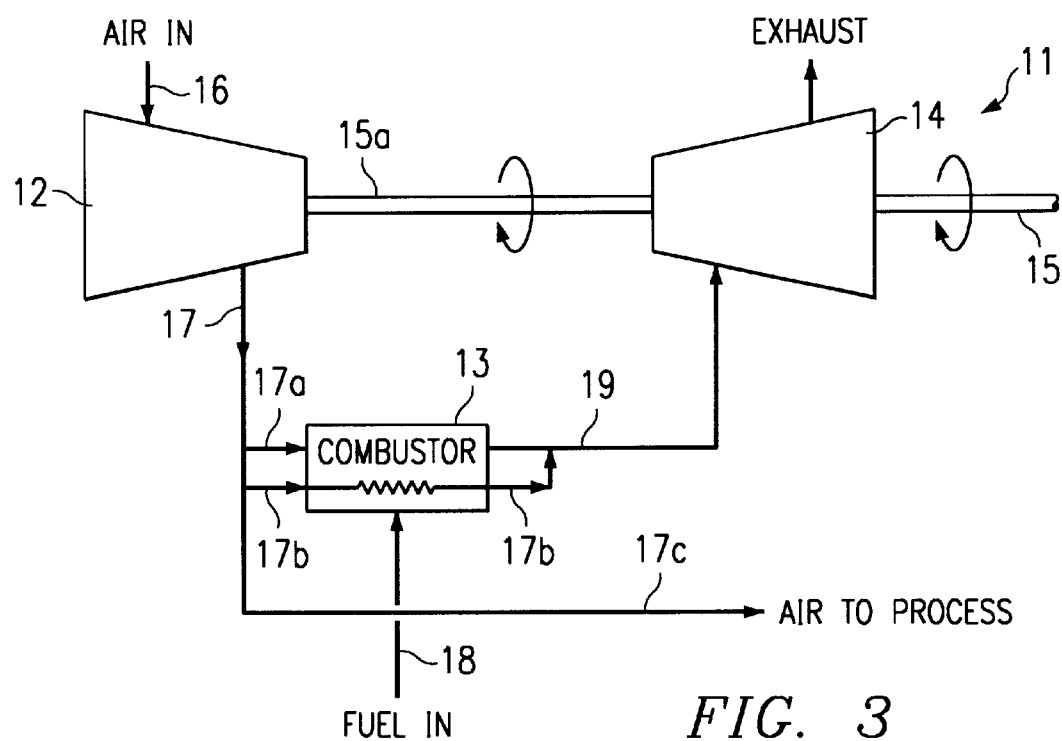
FIG. 3 is a schematic representation of the gas turbine of FIG. 2 as operated in accordance with the present invention.

Referring to FIG. 3, a portion of the compressed air from section 12 (i.e. combustion air) is fed to the combustor 13 through line 17a where it is mixed with fuel from line 18 and another portion of the compressed air (i.e. cooling air) is passed through line 17b to cool the combustion gases from combustor 13 similarly as described above. Again, the fuel in line 18 is tail gas which is recovered within system 10 as be further discussed below. The remainder of the compressed air air (e.g. about 30–40% of total flow) from compressor section 12 of turbine 11 which is not needed for combustion-cooling is supplied through line 17c as "process air" directly to process-air compression unit 20 which, in turn, is comprised of one or more compression stages 21 (four shown). Compression unit 20 provides the "process-air" to carry out the present gas conversion process.

The primary "process-air" is supplied to compression unit 20 at ambient conditions through inlet 20a. However, by using the portion of the compressed, combustion-cooling air from compressor section 12 which is not needed for combustion/cooling in turbine 11 to make up part of the process-air needed to carry out the present process, the horsepower required for compressor unit 20 may be reduced as much as 20–30% from that which otherwise would be needed.

As before, the combustion gases from combustor 13 are expanded through power turbine section 14 to drive the turbine which, in turn, drives both the compressor section 12 of turbine 11 through shaft 15a and all of the compression stages 21 of unit 20 through output shaft 15, as will be understood in the art. The exhaust from turbine 14, in turn, is passed through exchanger 22 wherein substantially amounts of heat (e.g. as much as 93 MMBTUs per hour) can be transferred into feed water in line 23 to thereby generate steam for use within the process or for use in auxiliary applications (not shown).

Compressed process-air (e.g. about 600 psia and 328° F.) exits compression unit 20 through line 25 and is mixed with superheated steam (e.g. about 1200 psia and 900° F.) from line 24. The air/steam mixture is further heated in furnace 26 (which can also be fired by the tail gas from the process) to about 1000° F. and reaches a pressure of about 595 psia before the process-air/steam stream is delivered to Autothermal Reforming Unit ("ATR") 27. Feed gas (e.g. natural gas at about 610 psi and 100° F.) flows through the inlet of line 28 and is (a) heated in furnace 26, (b) passed through hydrogen sulfide removers 29 (two shown), and (3) re-heated in furnace 26 to reach a temperature about 1000° and a pressure of about 595 psia before it is delivered to ATR 27 through line 28.

As will be understood in the art, ATR 27 may take different forms but generally is comprised of a vessel having a reforming catalyst (e.g. nickel-containing catalyst) therein which converts the air/steam/natural gas to a synthesis gas "syngas" (i.e. CO and $H_2$); e.g. see U.S. Pat. No. 4,973,453. The syngas along with nitrogen and unreacted light hydrocarbons leave ATR 27 through outlet 30 at about 590 psi and 1806° F. and is cooled in (a) exchangers 31 and 32 to about 600° F., (b) exchanger 33 to about 336° F., and (c) cooler 34 to about 100° F. (optional) before being delivered to separator 35 where any condensed water is removed through outlet 36*a*.

The syngas then flows from separator 35 through exchanger 33 in line 36 where it is heated to about 415° F. (565 psia) before it is delivered to the Fischer-Tropsch ("F-T") reactor 37. Again, as will be understood in the art, F-T reactors of this type are well known in the art and basically comprised of a vessel containing an appropriate catalyst (e.g. cobalt-containing catalyst) therein. There are several known catalysts which are used in converting a synthesis gas depending on the product desired; e.g., see U.S. Pat. Nos. 4,579,985 and 4,579,986.

The product (about 415° F., 535 psia) flows from F-T reactor 37 at about 535 psia and 415° F. through two separate outlets 38, 39. The product in outlet 38 is first cooled in exchanger 40 to about 309° F. and then in cooler 41 to about 100° F. before it is delivered to the first separator 42*a* in a first row of separators 42*a*–*d* in separator section 42. The series of separators reduce the pressure of the product in increments from about 525 psia to about 15 psia before the product is sent through outlet line 43 to storage or for further processing (e.g. hydrocracking) or for other use. Tail gas (uncondensed light hydrocarbons, nitrogen, etc.) is taken off the first separator 42*a* at about 520 psia through line 44 and is passed through exchanger 40 to cool the product in line 38 and to raise the temperature of the tail gas to about 350° F. In some applications, the tail gas may be expanded through power turbine 44 to reduce its pressure and to recover mechanical power, e.g. drive an electrical generator 45 or the like. Any condensed water is removed from separator 42*a* through line 50.

Tail gas also flows from the second separator 42*b* through line 46 and is combined with the tail gas in line 44. The tail gas still has a good BTU value and can be used as fuel within the process; e.g. fuel for the combustor 13 in turbine 11 (line 44*a*, line 18); furnace 26 (line 44*b*), etc. Any remaining tail gas in line 44 can be used or sold as a particular situation dictates. Any gas remaining in the product once it has reached separators 42*c*, 42*d* is likely to be at too low of pressure to be used as fuel within the process so it is carried through line 47 to a flare 48 or for similar disposal.

The product in the other outlet line 39 is delivered to a first separator 42*e* in a second row of separators 42*e*–*g* in separator section 42 and undergoes stepped-pressure reduction before it is delivered to storage through line 55. Any gas which separates from the product in separators 42*e*–*g* is conveyed to respective separators in the first row through lines 52 and is accordingly processed. Water which separates from the product in separator 42*e* is removed through line 53 and is combined with the water in line 50 for disposal at outlet 56.

In accordance with the present invention, heat is recovered and utilized at almost every station within the system. That is, two utilities loops are provided which generate steam and recover excess energy from the system as the process is being carried out. Referring again to the FIG. 1, boiler feed water is delivered under high pressure (e.g. about 1200 psia) into the first utilities loop 60 through "make-up" inlet 61 and is raised to about 350° F. as it passes through exchanger 62.

A split stream of heated water is taken from line 60 through line 63 and is passed through heat exchangers 31 and 32 to recover heat from the product leaving ATR 27 thereby raising the temperature of the water (now superheated steam) to about 900° before it is returned to line 60. A portion of the superheated steam can be directed (a) through line 24 into the compressed, process-air in line 25 and (b) through line 28*a* to heat the feed gas in line 28.

The remainder of the heated water is passed through boiler 64 and superheater 65 in line 60 (both of which can be fueled by tail gas) to raise its temperature to about 900° before being recombined with the steam from line 63 which is also at the same temperature and pressure. The steam is then expanded through turbine 66 to covert the recovered heat to usable mechanical power (e.g. drive electrical generator 67 or the like).

The second utilities loop 70 is comprised of line 70 wherein make-up water is delivered to loop 70 through inlet 71. The water flows into F-T reactor 37 through line 72 at a temperature of about 390° and out line 73 at a temperature of about 415° F. The water is then flowed through exchanger 62 where the heat recovered from reactor 27 is transfered to the boiler feed water in loop 60 thereby adding to the overall efficiency of the process.

The above describes a system and a process for converting natural gas or the like to syngas which, in turn, is then converted into a liquid hydrocarbon product wherein most of the heat generated in the process is recovered for use in the process or is converted to mechanical energy. Also, the tail gas generated in the process is used as the primary fuel required in the process. Further, the turbine used to compress the process-air is operated to provide a portion of the required process-air, itself.

What is claimed is:

1. In a Fischer-Tropsch conversion process for converting a hydrocarbon gas to a liquid hydrocarbon wherein a gas turbine is used to drive a compressor unit which compresses air which, in turn, is mixed with said hydrocarbon gas and steam and is flowed through a first reactor with a first catalyst to produce a syngas which is flowed through a second reactor with a second catalyst to produce said liquid hydrocarbon and a tail gas; said gas turbine having a compressor section, a combustor and a turbine section, the improvement comprising:

compressing air in said compressor section of said gas turbine;

supplying a first portion of said compressed air from said compressor section of said gas turbine to said combustor;

supplying said tail gas from said conversion process as a fuel to said combustor to mix with said first portion of said compressed air from combustion in said combustor thereby producing combustion gases in said combustor;

mixing a second portion of said compressed air from said compressor section of said gas turbine with said combustion gases from said combustor of said gas turbine to cool said combustion gases before said combustion gases are expanded through said turbine section of said gas turbine; and supplying the remaining portion of said compressed air from said compressor section of said gas turbine directly to said first reactor of said conversion process for use as process air in said conversion process.

2. The method of claim 1 wherein said remaining portion of said compressed air comprises about 30% to about 40% of the total volume of air compressed in said compressor section of said gas turbine.

3. The method of claim 1 wherein said tail gas produced in said conversion process is comprised of methane, carbon monoxide, carbon dioxide, hydrogen, and nitrogen.

4. The method of claim 1 wherein said improvement further includes:

recovering heat from said combustion gases from said combustor after said gases have passed through said turbine section of said gas turbine.

* * * * *

UNITED STATES PATENT AND TRADEMARK OFFICE
CERTIFICATE OF CORRECTION

PATENT NO. : 6,172,124 B1
DATED : January 9, 2001
INVENTOR(S) : John R. Wolflick, et al.

Page 1 of 1

It is certified that error appears in the above-identified patent and that said Letters Patent is hereby corrected as shown below:

<u>Title page,</u>
Item [73], Assignee, delete "Sybtroleum Corporation" and insert
-- Syntroleum Corporation --
Item [56], References Cited, after "4,528,811  7/1985  Stahl", insert
-- 4,549,396  10/1985  Garwood et al. --

<u>Column 1,</u>
Line 44, after "Nos.", delete "5"
Line 57, after "for", delete ","

<u>Column 2,</u>
Line 14, before "combustion", insert -- " -- and after "air" -- " --
Line 42, after "cooling", delete "air"

<u>Column 4,</u>
Line 25, after "pressed", delete "air"
Line 31, after "air"", insert -- needed --

Signed and Sealed this

Twenty-seventh Day of November, 2001

*Attest:*

NICHOLAS P. GODICI
*Attesting Officer*     Acting Director of the United States Patent and Trademark Office